(12) United States Patent
Glard et al.

(10) Patent No.: US 10,349,954 B2
(45) Date of Patent: Jul. 16, 2019

(54) SURGICAL NAVIGATION SYSTEM

(71) Applicants: Yann Glard, Marseilles (FR); Vincent Pomero, Gardanne (FR)

(72) Inventors: Yann Glard, Marseilles (FR); Vincent Pomero, Gardanne (FR)

(73) Assignee: PYTHEAS NAVIGATION, Marseilles (FR)

( * ) Notice: Subject to any disclaimer, the term of this patent is extended or adjusted under 35 U.S.C. 154(b) by 0 days.

(21) Appl. No.: 15/538,994

(22) PCT Filed: Dec. 22, 2015

(86) PCT No.: PCT/FR2015/053735
§ 371 (c)(1),
(2) Date: Jun. 22, 2017

(87) PCT Pub. No.: WO2016/102898
PCT Pub. Date: Jun. 30, 2016

(65) Prior Publication Data
US 2017/0354426 A1 Dec. 14, 2017

(30) Foreign Application Priority Data
Dec. 23, 2014 (FR) .................................... 14 63223

(51) Int. Cl.
*A61B 17/17* (2006.01)
*A61B 34/20* (2016.01)
(Continued)

(52) U.S. Cl.
CPC .......... *A61B 17/1757* (2013.01); *A61B 90/10* (2016.02); *A61B 90/37* (2016.02);
(Continued)

(58) Field of Classification Search
CPC .............. A61B 17/701; A61B 17/7044; A61B 17/7055; A61B 90/10; A61B 90/37;
(Continued)

(56) References Cited

U.S. PATENT DOCUMENTS 5,141,512 A * 8/1992 Farmer ............. A61B 17/1746
606/87
8,419,746 B2 4/2013 Bourlion et al.
(Continued)

FOREIGN PATENT DOCUMENTS

DE 695 34 862 T2 8/2006
EP 2 719 353 A1 4/2014
(Continued)

OTHER PUBLICATIONS

International Search Report, dated Mar. 29, 2016, from corresponding PCT application No. PCT/FR2015/053735.

*Primary Examiner* — Pedro Philogene
(74) *Attorney, Agent, or Firm* — Young & Thompson (57) ABSTRACT

Embodiments of the invention relate to an ancillary surgical instrument including at least a first contact point to come into contact with a first reference point of an operating area; a second contact point intended to come into contact with a second reference point of the operating area; a contact area intended to come into contact with a third reference point of the operating area; a determination unit for determining an orientation reference of the ancillary instrument in a Galilean orientation reference; and a communication unit for communication the determined orientation reference.

18 Claims, 6 Drawing Sheets

(51) Int. Cl.
*A61B 90/00* (2016.01)
*A61B 90/10* (2016.01)

(52) U.S. Cl.
CPC ............... *A61B 2034/2048* (2016.02); *A61B 2034/2051* (2016.02); *A61B 2034/2055* (2016.02); *A61B 2034/2068* (2016.02); *A61B 2090/068* (2016.02); *A61B 2090/3937* (2016.02); *A61B 2090/3983* (2016.02)

(58) Field of Classification Search
CPC .... A61B 2034/2048; A61B 2034/2051; A61B 2034/2055; A61B 2034/2068; A61B 2090/068; A61B 2090/3937; A61B 2090/3983
USPC ........ 606/86 A, 86 R, 34, 40, 246–289, 546, 606/547, 87, 89, 91
See application file for complete search history.

(56) References Cited

U.S. PATENT DOCUMENTS

| | | |
|---|---|---|
| 2010/0036384 A1 | 2/2010 | Gorek et al. |
| 2017/0007328 A1 | 1/2017 | Cattin et al. |

FOREIGN PATENT DOCUMENTS

| | | | | |
|---|---|---|---|---|
| EP | 2719353 | * | 4/2014 | ............. A61B 90/10 |
| EP | 2 901 957 | | 8/2015 | |
| EP | 2 023 811 | | 8/2018 | |
| KR | 2006 0003685 A | | 1/2006 | |
| KR | 20060003685 | * | 1/2006 | ......... A61B 17/1757 |
| WO | 96/11624 A2 | | 4/1996 | |
| WO | WO96/11624 | * | 4/1996 | ......... A61B 17/1757 |
| WO | 2006/109983 A1 | | 10/2006 | |
| WO | WO2006/109983 | * | 10/2006 | ............. A61B 17/1757 |
| WO | 2014/176207 A1 | | 10/2014 | |
| WO | WO2014/176207 | * | 10/2014 | ............. A61B 90/10 |

* cited by examiner

SURGICAL NAVIGATION SYSTEM

CROSS-REFERENCE TO RELATED APPLICATION

This application claims the benefit under 35 U.S.C. § 119(a)-(d) of French Patent Application No. 14 63223, filed on Dec. 23, 2014 and entitled "Système d'Orientation Chirurgical". The above cited patent application is incorporated herein by reference in its entirety.

FIELD OF THE INVENTION

The present invention relates to a surgical orientation system and an ancillary instrument that can be used within the scope of such a system.

The internal skeletal structure of a mammal, human or animal, is sometimes composed of about a hundred bones. The spinal column is a chain of bones or vertebrae allowing a certain flexibility and movement, while protecting the nerve and vascular structures inside and around the spinal column. The spinal column starts at the base of the skull, extends to the pelvis and is composed of four regions—cervical, thoracic, lumbar and pelvic.

Figure 1A:
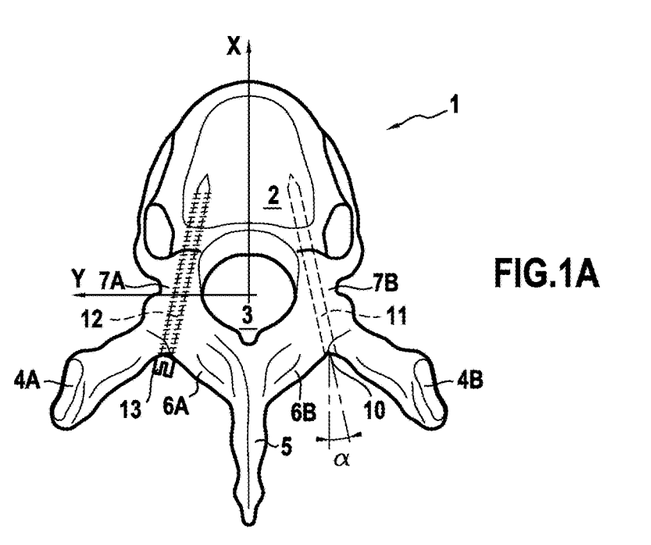
FIGS. 1A, 1B, previously described, respectively show a top view and a side view of a typical vertebra.
Figure 1B:
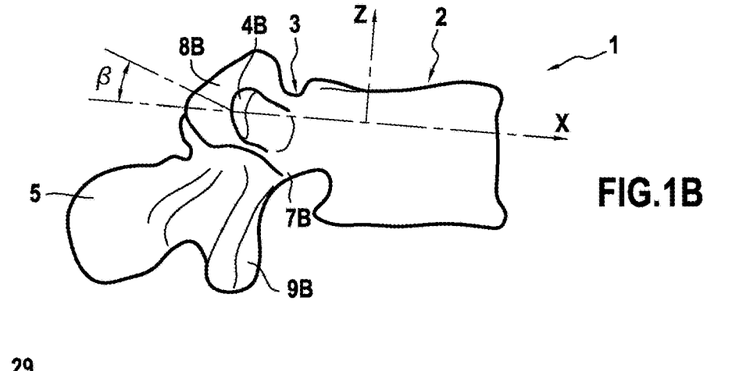

FIGS. 1A, 1B show respectively a top view and a side view of a typical vertebra 1. The vertebra 1 comprises: a vertebral body 2 orientated towards the front; a vertebral foramen 3 in the form of a hole allowing the spinal cord to pass through; two transverse processes 4A, 4B, orientated towards the back and outwards; a spinous process 5 between the transverse processes 4A, 4B and orientated downwards; two laminae 6A, 6B which connect the transverse processes 4A, 4B to the spinous process 5; two pedicles 7A, 7B which connect the vertebral body 2 to the transverse processes 4A, 4B; two upper articular facets 8A (not shown), 8B and two lower articular facets 9A (not shown), 9B which allow articulation of the vertebrae 1 between each other.

The normal or ideal vertebral alignment can be disturbed due to a trauma or a disease, for example scoliosis. The vertebrae can pivot about three axes (X, Y, Z), sometimes requiring a surgical operation in order to correct the anomalies and re-establish an ideal, or at the very least a better, alignment of the spinal column.

In this case, at least two adjacent vertebrae 1 are generally fused together by a process in which a surgeon opens the patient, generally via the back, determines an entry point 10 and drills holes 11 into the pedicles 7A, 7B of the vertebrae 1. The holes are drilled with an axial angle alpha α (the angle with respect to the plane XZ) and a sagittal angle beta β (the angle with respect to the plane XY), shown in FIGS. 1A, 1B respectively.

Then, the pedicle screws 12 comprising U-shaped ends 13 are inserted into the holes 11. (For reasons of clarity in FIG. 1A, a single entry point 10, hole 11, pedicle screw 12, and end 13 are shown.) The ends 13 receive connecting elements (not shown), for example bars, which make it possible to reduce deformation and fuse the vertebrae 1 together.

Then, the connecting elements are connected between the pedicle screws of two adjacent vertebrae 1 in order to correct, gradually, the alignment of the spinal column, which is based on the approximate correction objectives for each level of the spinal column and are derived from medical images (electromagnetic 'X' rays, tomodensitometry, magnetic resonance imaging, etc.) taken preoperatively, i.e. before a surgical operation. As a result, all the drilled holes 11 and the pedicle screws 12 placed in the vertebrae 1 must be carefully positioned and aligned in order not to damage the adjacent nerve and vascular structures, or even cause the death of the patient. At the very least, a second operation would have to be carried out, involving additional costs and risks.

Guidance systems have been developed to aid the surgeon to drill the holes 11 in the vertebra 1 and accurately place the pedicle screws 12.

The article "Guided pedicle screw insertion and training" by Manbachi et al. describes a surgical orientation system based on optoelectronic orientation. Tomodensitometry, or TDM, is a medical imaging technique carried out during a preoperative phase in order to construct a three-dimensional model of the area to be operated on, for example one or more vertebrae. During a perioperative phase, i.e. the actual operation, optical markers arranged on the surgical tools are captured by a plurality of cameras which film the operating theatre in real time, in order to reference the positions of the tools with respect to the model.

Moreover, the patient is generally lying on the back when the images are taken, whereas they are lying on the front for the operation. As a result, the positions of the vertebrae do not correspond between the images taken and the position of the patient during the operation.

Finally, such a system is expensive, bulky in an operating theatre and can lack accuracy if for example certain markers are obscured during the operation. In the case of a system which relies on imaging taken during the perioperative phase, the personnel and the patient are exposed to electromagnetic rays (X rays) and the duration of the operation is longer.

The U.S. Pat. No. 8,419,746 describes a surgical tool comprising a rod, at least two electrodes arranged on the rod, and means for measuring the impedance between the electrodes. A change in impedance indicates an empty space, which means that the end of the rod has come out of the bone. Nevertheless, such a tool does not allow the surgeon to determine the ideal path, it only signals an incorrect path after the fact, which can be too late.

As a result, a need exists for systems and tools for indicating beforehand to the surgeon the correct path with respect to the images taken preoperatively and the position of the patient during the operation.

SUMMARY OF THE INVENTION

Embodiments of the invention relate to an ancillary surgical instrument comprising at least:
  a first contact point intended to come into contact with a first reference point of an operating area;
  a second contact point intended to come into contact with a second reference point of the operating area; and
  a contact area intended to come into contact with a third reference point of the operating area;
The ancillary instrument moreover comprises:
  a means for determining an orientation reference of the ancillary instrument in a Galilean orientation reference; and
  a means for communicating the determined orientation reference.

According to an embodiment, the first contact point, the second contact point, the contact area, the determination means and the communication means are incorporated into a single part of the ancillary instrument.

According to an embodiment, the first contact point, the second contact point and the contact area are incorporated into a first part of the ancillary instrument, and the determination means and the communication means are incorporated into a second part which can be fitted onto the first part.

According to an embodiment, the contact area is an essentially planar tangential area.

According to an embodiment, the orientation reference of the ancillary instrument allows an orientation reference of the operating area to be determined with respect to the Galilean orientation reference by means of a rotation matrix.

According to an embodiment, the ancillary instrument is in the form of a compass and comprises:
- at least two branches at the lower ends of which the first point and the second point are arranged; and
- a third branch at the lower end of which the tangential contact area in the form of a palpation plate is arranged.

According to an embodiment, the ancillary instrument is in the form of a Y and comprises:
- at least two branches at the ends of which the first point and the second point are arranged in the form of straight edges;
- a third branch in the form of a handle; and
- a central area having a lower face which forms the tangential contact area.

According to an embodiment, the ancillary instrument moreover comprises means for validating the tangential contact area.

According to an embodiment, the tangential contact area is transparent and arranged in a cross-ruled form and marked in order to allow a surgeon to determine where exactly the tangential area is in contact with the third reference point.

According to an embodiment, the length, the angle, and/or the inclination of at least one branch of the ancillary instrument can be adjusted.

According to an embodiment, the first point, the second point, and the tangential contact area are coplanar.

According to an embodiment, the means for determining the orientation reference is a device comprising at least one of the following components:
- a tri-axial accelerometer;
- a tri-axial magnetometer; and/or
- a tri-axial gyroscope.

According to an embodiment, the means for determining the orientation reference is a device comprising at least three non-aligned optical markers, intended to be visible by at least one camera filming the operating area.

According to an embodiment, the means for communicating the orientation reference is a visual display.

According to an embodiment, the means for communicating the orientation reference is a wired or wireless connection.

Embodiments of the invention moreover relate to an assembly comprising at least two ancillary instruments according to the invention, the ancillary instruments being designed for operating areas that are different from one another.

Embodiments of the invention moreover relate to a surgical orientation system comprising at least one ancillary instrument according to the invention and a surgical tool comprising:
- means for determining an orientation reference of the tool; and
- means for communicating the orientation reference of the tool.

According to an embodiment, the ancillary instrument and the surgical tool are capable of being coupled to one and the same device for determining and communicating the orientation reference.

Embodiments of the invention moreover relate to an operating theatre equipped with an ancillary surgical instrument according to the invention and a device for displaying images and data processing comprising:
- a screen for displaying images taken of the operating area;
- a processor;
- means for entering and manipulating data; and
- means for receiving data communicated by the ancillary instrument.

Embodiments of the invention moreover relate to a process for the preoperative preparation of a surgical operation, comprising the steps of:
- taking at least one three-dimensional image of an operating area;
- determining at least three reference points of the operating area from the three-dimensional image;
- calculating an orientation reference by means of the reference points, the orientation reference being identifiable subsequently by an ancillary instrument according to the invention; and
- determining at least one local reference for the surgical movement to be performed.

Embodiments of the invention moreover relate to a non-transitory medium which can be read by a computer and comprising a program of computer-executable instructions for carrying out the process according to the invention.

BRIEF DESCRIPTION OF THE DRAWINGS

Other particular characteristics and advantages of the present invention will become apparent from the detailed description given with reference to the figures in which.

DETAILED DESCRIPTION OF THE INVENTION

Figure 2A:
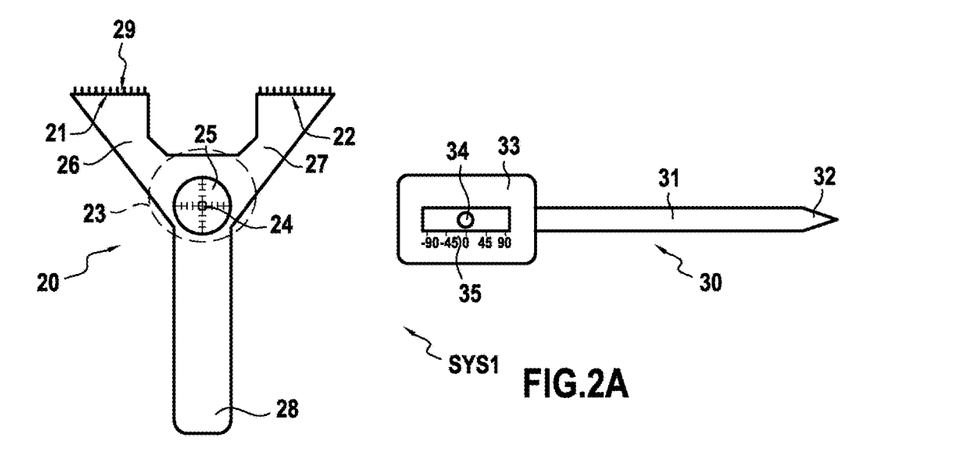
FIG. 2A shows a top view of a surgical orientation system comprising an ancillary surgical instrument and a surgical tool according to an embodiment.

FIG. 2A shows a surgical orientation system SYS1 according to an embodiment. The system SYS1 comprises a tool 20 (hereafter "ancillary instrument") and a surgical tool 30, for example for drilling.

The ancillary instrument 20 comprises: at least two contact points 21, 22; a planar tangential contact area 23; a means 24 for determining an orientation reference RA of the ancillary instrument and a means 25 for communicating the orientation reference RA of the ancillary instrument. The orientation reference RA of the ancillary instrument 20 can be compared to an orientation reference RO of an operating area ZO (for example the vertebra 1) and as a result makes it possible to know the orientation reference RO in a Galilean orientation reference RS, for example of an operating theatre ZS (shown in FIG. 8). Hereinafter, the term orientation reference RO of the operating area will be used.

In this embodiment, the ancillary instrument 20 is in the form of a Y, the points 21, 22 being straight edges of a first branch 26 and of a second branch 27 respectively, and a third branch 28 serving as a handle. The branches 26, 27 are the upper left and right ends of the Y respectively, the branch 28 is the lower central end of the Y, and the area 23 is arranged at the center of the Y and comprises a lower face that is more or less planar. The ancillary instrument 20 further comprises "spikes" 29 on the points 21, 22 which prevent the ancillary instrument 20 from sliding once in contact with the vertebra. The points 21, 22 and the contact area plane 23 are coplanar.

Figure 2B:
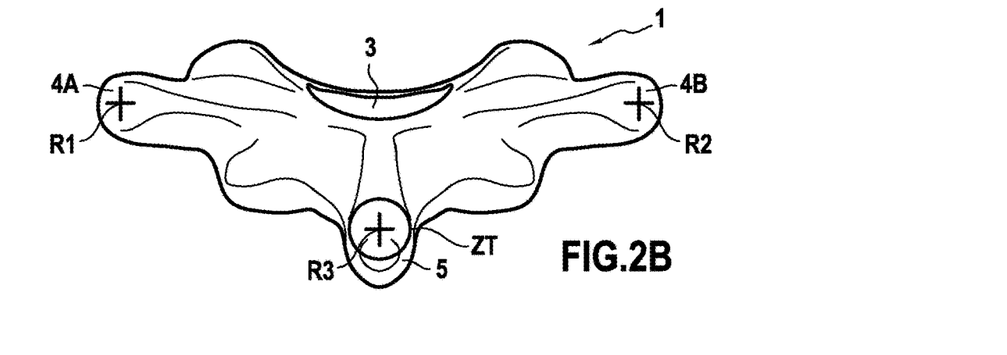
FIG. 2B shows a vertebra with the reference points for the operation.

As shown in FIG. 2B, the operating area ZO (here the vertebra 1) comprises at least three reference points R1, R2, R3. In the case of a vertebra 1, the points R1, R2 are arranged for example at the top of the transverse processes 4A, 4B respectively, and are quite easy to locate with the naked eye, in particular by an experienced surgeon. The point R3 is arranged on the spinous process 5 in a tangential area ZT, as will be explained below. As a result, the contact points 21, 22 are each intended to come into contact with the points R1, R2 respectively and the area 23 is placed on the point R3 in order to determine a system of coordinates or "orientation reference" RO of the operating area ZO with respect to the orientation reference RS of the operating theatre ZS.

The surgical tool 30 is for example a tool for drilling the vertebra 1, and comprises: a rod 31; a point 32 at the front end of the rod; a handle 33; a means 34 for determining an orientation reference RT of the instrument; and a means for communicating the orientation reference RT of the instrument.

In the simplest case, the determination means 24, 34 are levels, also known as bubble levels, and the communication means 25, 36 are visual indicators, for example figures marked around the spirit or even a simple circle at the center of the level.

Figure 3A:
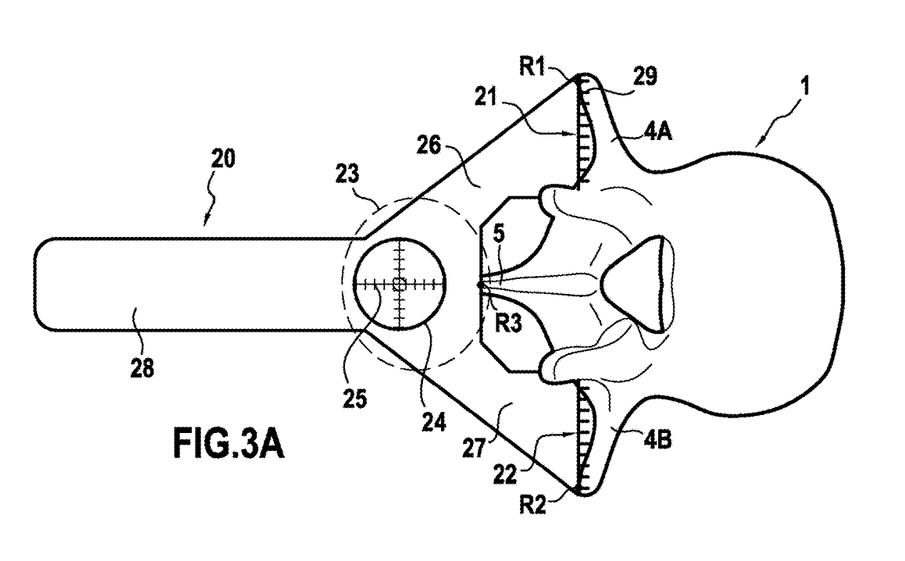
FIGS. 3A, 3B show respectively a top view and a side view of the ancillary surgical instrument shown in FIG. 2A in use.
Figure 3B:
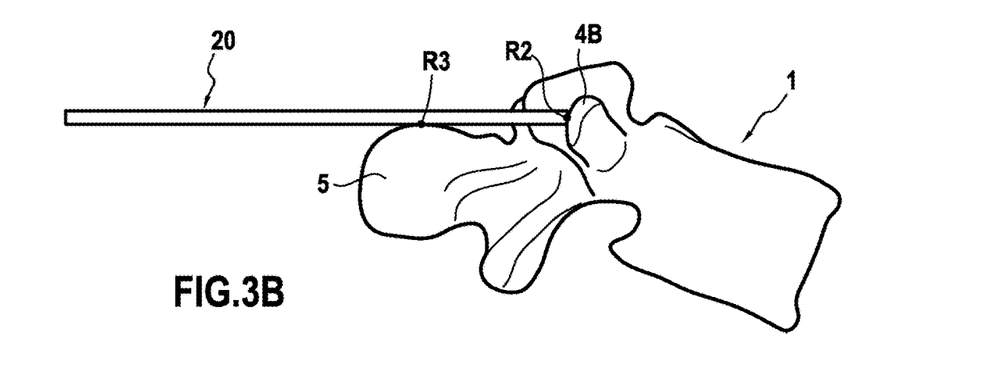

FIGS. 3A, 3B show respectively a top view and a side view of the ancillary instrument 20 placed on a vertebra 1. The dimensions of the ancillary instrument 20 are adapted to the application envisaged, for example approximately 10 cm in width, 15 cm in length, and 0.50 cm thick for operations on the human spinal column.

In a preoperative phase, images are obtained, for example of the entire spinal column, in order to make three-dimensional reconstructions of the operating area. Then, for each vertebra, the reference points R1, R2, R3 are determined, in order to define the orientation reference RO of the operating area. In certain embodiments, the point R3 is a point in the tangential area ZT, which will be more difficult to determine with the naked eye but will be contacted by the contact area 23 by simply placing the ancillary instrument on the area ZT.

Then, to place pedicle screws, the entry of the optimum screwing directions of the pedicle screws 12 makes it possible to define a direction vector for each pedicle screw.

Figure 4:
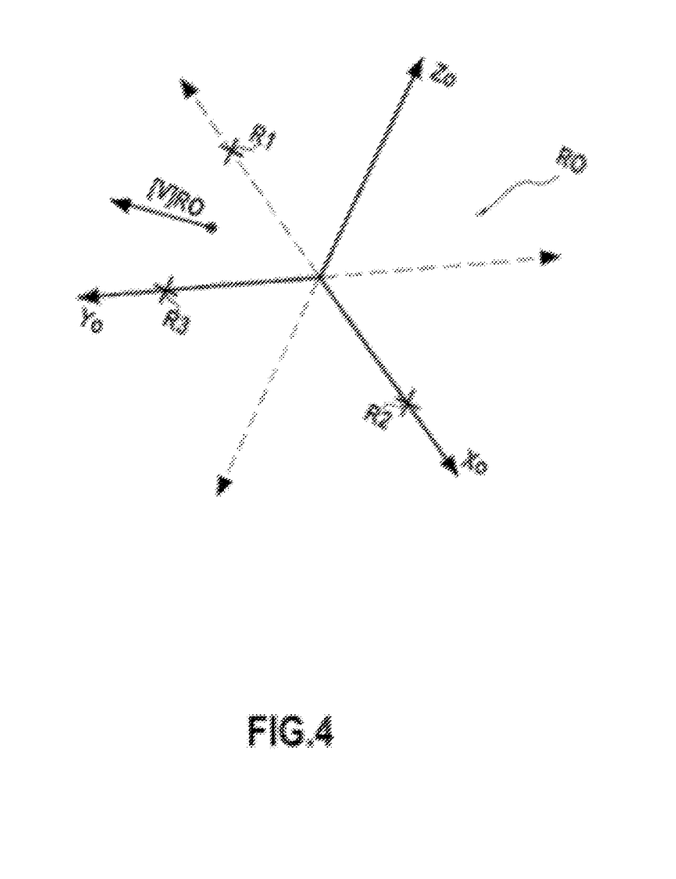
FIG. 4 shows an orientation reference of an operating theatre and an orientation reference of an operating area.

With reference to FIG. 4, which shows the orientation reference RO of the operating area and the Galilean orientation reference RS of the operating theatre, each orientation reference RO, RS comprises three axes, Xo, Yo, Zo; Xs, Ys, Zs respectively. An arrow [V]ro (or "local reference") shows a direction vector V for a surgical movement (for example placing a pedicle screw) expressed in the orientation reference RO of the operating area (currently in the vertebra). The orientation reference RO of the operating area is not necessarily aligned with the orientation reference RS of the operating theatre, as shown in FIG. 4.

Then, during the perioperative phase, the surgeon positions the ancillary instrument 20 on the vertebra 1, as shown in FIGS. 3A, 3B, by putting the points 21, 22 in contact with the reference points R1, R2 respectively, and then placing the area 23 on the reference point R3. The orientation reference RO of the operating area ZO is then determined with respect to the orientation reference RS of the operating theatre, using the determination and communication means 24, 25 of the orientation reference RO of the operating area ZO.

A rotation matrix Mrors, which expresses the orientation reference RO in the orientation reference RS, is defined. A direction vector [V]rs in the orientation reference RS of the operating theatre ZS can be established with respect to the orientation reference RO of the operating area ZO, established beforehand according to the following equation:

$$[V]rs = Mrors \cdot [V]ro \qquad \text{[equation 1]}$$

Finally, the surgical tool 30 determines and communicates, using the determination and communication means 34, 35 of the orientation reference RT of the instrument, its orientation in real time, in particular the orientation of its rod 31, in the orientation reference RS of the operating theatre. The dynamic orientation of the rod 31 with respect to the ideal orientation of the pedicle screw to be placed, allows the surgeon to adapt the orientation of the tool 30 to make it correspond to the orientation of the direction vector [V]ro expressed in the Galilean orientation reference RS (i.e. [V]rs).

Figure 5A:
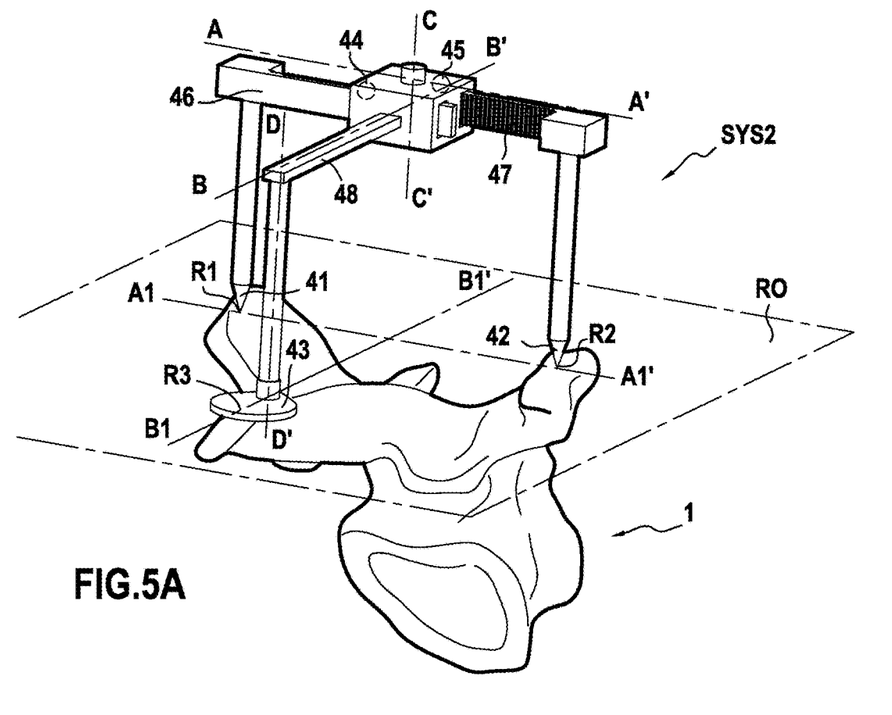
FIGS. 5A, 5B show respectively a perspective view and a top view of a surgical orientation system according to another embodiment.
Figure 5B:
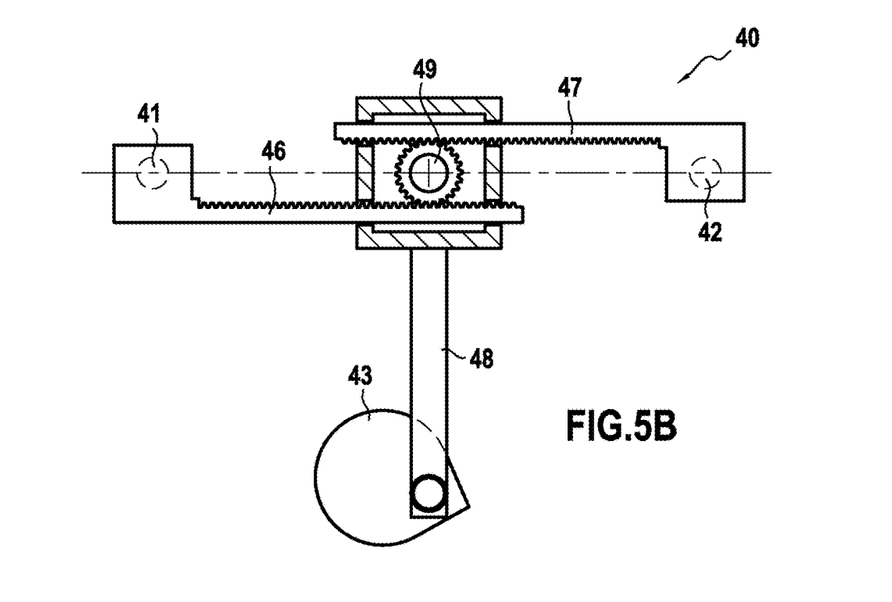

FIGS. 5A, 5B show respectively a perspective view and a top view of a surgical orientation system SYS2 according to another embodiment. The system SYS2 comprises an ancillary instrument 40 and a surgical tool (not shown for reasons of simplicity). The ancillary instrument 40 comprises: at least two contact points 41, 42; a tangential contact area or "planar palpation plate" 43; a means 44 for determining the orientation reference RA (and as a result RO) and a means 45 for communicating the orientation reference (not shown in detail).

In this embodiment, the ancillary instrument 40 is in the form of a "compass", the points 41, 42 being the lower ends of the branches 46, 47 arranged according to a transverse axis A-A', and the contact area 43 being arranged at the lower end of a third branch 48 arranged along a longitudinal axis B-B' which bisects the axis A-A' at a central vertical axis C-C' and also serves as a handle.

In this embodiment, the determination means 44 is a "MEMS" or "microelectromechanical system" which determines the plane of the ancillary instrument. This means can comprise a tri-axial accelerometer, a tri-axial magnetometer, and/or a tri-axial gyroscope, as known to a person skilled in the art and thus not explained in more detail. The communication means 45 is a wired (cable) or wireless (contactless) connection, for example by Wi-Fi or Bluetooth.

It will be noted that the vertebrae on which it is possible to operate can vary with respect to the "typical" vertebra shown in FIG. 1, depending on the reason for the operation, the age of the patient, their morphology, etc. As a result, the reference points R1, R2, R3 can be found offset with respect to the standard reference points. In this case, it is desirable to be able to adjust the ancillary instrument so that the reference points R1, R2, R3 can be contacted by the ancillary instrument.

In this embodiment, the lengths of the branches 46, 47 can be adjusted along the axis A'A' in order to take possible variations in the size of the vertebrae into account. To this end, the ancillary instrument comprises a pinion 49 for adjusting the lengths of the branches 46, 47, which make up the adjustment rails.

Moreover, it will be noted that in FIGS. 5A, 5B, the contact area 43 is articulated about a vertical axis D-D' at the distal end of the branch 48.

In other embodiments, the length of the branch 48 can be adjusted along the axis B-B' for example using a "telescopic" system, as well as the angles of the branches 46, 47, 48 with respect to the center, the inclination of the branches with respect to the plane formed by the axes A-A', B-B', etc.

In FIG. 5A, the ancillary instrument 40 is placed on a vertebra 1 in the perioperative phase. Firstly, the points 41, 42 of the branches 47, 48 are placed on the reference points R1, R2. An axis A1-A1' is formed between the points. If necessary, the distance between the points 41, 42 is modified by the pinion 49. Then, the ancillary instrument is pivoted about the axis A1-A1' so that the contact area 43 is placed on the point R3. The points 41, 42 and the contact area 43 are then coplanar.

An axis B1-B1' bisects the axis A1-A1' and the contact area 43. The orientation reference RO of the operating area ZO is determined by the determination means 44 and communicated outside the ancillary instrument 40 by the communication means 45.

Once the orientation reference RO is determined and communicated, the surgeon proceeds with drilling the holes using the surgical tool, which can be similar to the tool 30 described in relation to FIG. 2A, or can comprise MEMS determination and communication means which are wired or wireless (contactless), as described in relation to the ancillary instrument 40.

Figure 6:
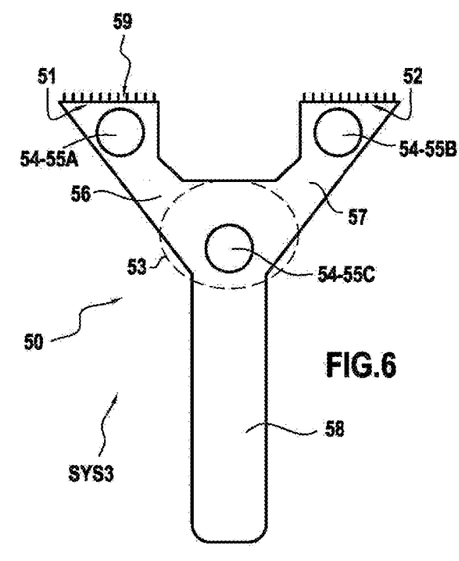
FIG. 6 shows a top view of a surgical orientation system according to another embodiment.

FIG. 6 shows a top view of a surgical orientation system SYS3 according to another embodiment. The system SYS3 comprises an ancillary instrument 50 and a surgical tool (not shown for reasons of simplicity).

The ancillary instrument 50 comprises: at least two contact points 51, 52; a tangential contact area 53; and determination and communication means 54-55A, 54-55B, 54-55C of the orientation reference RA (RO). The means 54-55A, 54-55B, 54-55C are non-aligned optical markers and intended to be captured by a plurality of cameras which film the operation theatre ZS in real time, in order to reference the positions of the tools with respect to the model.

Like the ancillary instrument 20 described in relation to FIG. 2A, in this embodiment, the ancillary instrument 50 is in the form of a Y, the points 51, 52 being straight edges of a first branch 56 and of a second branch 57 respectively, and a third branch 58 serving as a handle. The branches 56, 57 are the left and right upper ends of the Y respectively, the branch 58 is the central lower end of the Y and the area 53 is arranged in the center of the Y. The ancillary instrument 50 moreover comprises "spikes" 59 on the points 51, 52 which prevent the ancillary instrument 50 from sliding once in contact with the vertebra.

The surgical tool can be similar to the tool 30 described in relation to FIG. 2A (comprising levels), comprising MEMS determination and communication means which are wired or wireless (contactless) or even comprise optical markers.

Moreover, it is not obligatory that the surgical tool comprises such determination and communication means. In this case, it can be a simple standard surgical tool.

Figure 7:
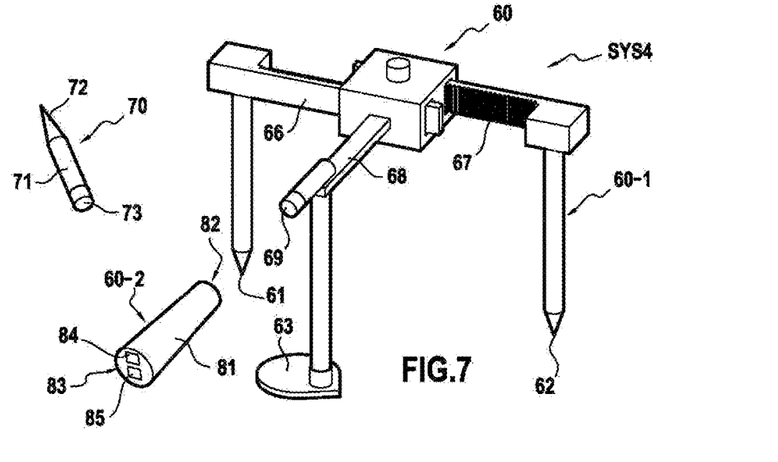
FIG. 7 shows a perspective view of a surgical orientation system according to another embodiment.

FIG. 7 shows a perspective view of a surgical orientation system SYS4 according to another embodiment. The system SYS4 comprises an ancillary instrument 60 and a surgical tool 70. In this embodiment, the ancillary instrument 60 is divided into two parts, a first part 60-1 for contact with the operating area, and a second part 60-2 for determining and for communicating the orientation reference of the operating theatre.

The first part 60-1 of the ancillary instrument 60 is similar to the ancillary instrument 40 described in relation to FIG. 5A, and comprises: at least two contact points 61, 62; a tangential contact area or "palpation plate" 63; branches 66, 67, 68; and an end 69 for receiving the second part 60-2.

The second part 60-2 comprises: a body 81; a hollow front end 82 for receiving the rear end 69 of the first part 60-1; a means 84 for determining the orientation reference RA, RT (RO) of the part 60-1 of the ancillary instrument 60; and a means 85 for communicating the orientation reference of the ancillary instrument 60.

The surgical tool 70 comprises: a rod 71; a point 72 at the front end of the rod; and an end 73.

Preferably, the ancillary instrument 60 and the surgical tool 70 cooperate so that the second part 60-2 of the ancillary instrument 60 can be fitted onto the first part 60-1 and the tool 70 in a non-permanent (it can be removed), accurate (no play between the elements) and repeatable manner. To this end, the ends 69, 73 of the first part 60-1 of the ancillary instrument 60 and of the surgical tool 70 respectively can comprise protuberances received in a notch inside the hollow front end 82, forcing the second part 60-2 to be fitted in a previously defined manner.

The second part 60-2 is firstly fitted onto the end 69 of the first part 60-1 of the ancillary instrument 60. Once the orientation reference RA is determined and communicated, the part 60-1 is put aside and the part 60-2 is removed and placed on the end of the surgical tool 70 in order to again determine and communicate the orientation reference RT of the tool 70. This system allows a reduction in cost as a single device for determining and communicating the orientation reference is necessary, and can be used in the case where the operating area is not likely to change position during operation.

Figure 8:
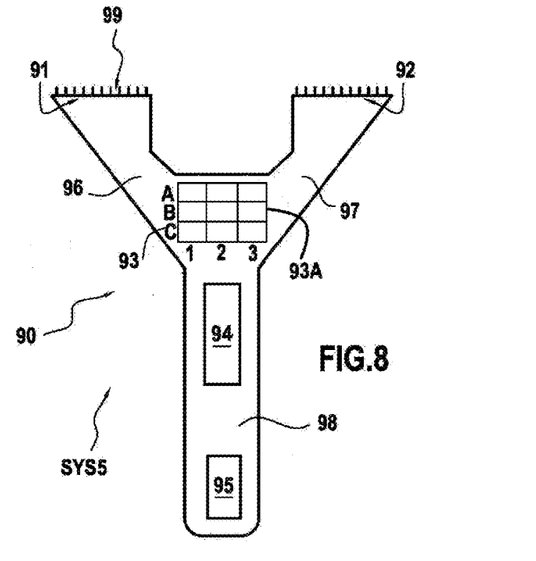
FIG. 8 shows a top view of a surgical orientation system according to another embodiment.

FIG. 8 shows a top view of a surgical orientation system SYS5 according to another embodiment. The system SYS5 comprises an ancillary instrument 90 and a surgical tool (not shown for reasons of simplicity).

The ancillary instrument 90 comprises at least two contact points 91, 92; a tangential contact area 93; means 94 for determining the orientation reference, for example an "MEMS" system as described in relation to FIG. 5A, and means 95 for communicating the orientation reference for example a wireless (contactless) connection.

Like the ancillary instrument 50 described in relation to FIG. 6, in this embodiment, the ancillary instrument 90 is in the form of a Y, the points 91, 92 being the straight edges of a first branch 96 and of a second branch 97 respectively, and a third branch 98 serving as a handle. The branches 96, 97 are the left and right upper ends of the Y respectively, the branch 98 is the central lower end of the Y and the area 93 is arranged at the center of the Y. The ancillary instrument 90 comprises moreover "spikes" 99 on the points 91, 92 which prevent the ancillary instrument 90 from slipping when in contact with the vertebra.

The ancillary instrument 90 comprises moreover means 93A for validating the tangential contact area 93. To this end, in this embodiment, the area 93 is transparent and arranged in a cross-ruled form and preferably marked for example with FIGS. 1 to 3) and letters (A to C), in order to allow a surgeon to determine exactly where the tangential area is in contact with the third reference point. For example, during the preoperative phase, it can be determined that the third reference point must be in contact with the area A3 of the tangential area. The spikes 99 can be also equipped with markers (not shown) in order to facilitate the referencing of the contact points.

In another embodiment, the validation means are a sensitive contact area which detects the contact with the third reference point, and communicates it for example by the communication means.

Figure 9:
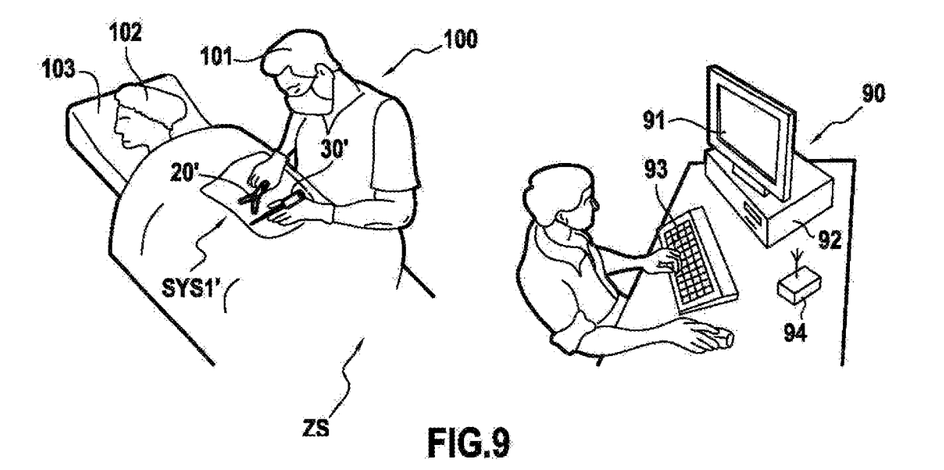
FIG. 9 shows an operating theatre equipped with a surgical orientation system according to an embodiment.

FIG. 9 shows a operating theatre ZS equipped with a surgical orientation system. By way of example, a system SYS1' is shown here, comprising an ancillary instrument 20' and a tool 30' equipped with the "MEMS" determination means and wireless communication means.

The operating theatre ZS is equipped with a device 90 for displaying images and for data processing, such as a computer. The device 90 comprises a screen 91, a processor 92, means for entering and manipulating data 93 (a keyboard, a mouse, a voice sensor, etc.), and means 94 for receiving the data communicated by the ancillary instrument 20' and/or the tool 30'.

The operating theatre comprises moreover an "operating entity" 100 comprising a surgeon 101 who operates on a patient 102 lying on an operating table 103.

The screen 91 makes it possible to display the images I obtained from the operating area ZO during the preoperative phase. The personnel of the operating suite, and particularly the surgeon, can consult the images during the operation. These images can be "static" or advantageously "dynamic". By "dynamic", is meant that the orientation references of the ancillary instrument 20' and/or of the surgical tool 30' are determined, communicated to the computer 90, and displayed on the screen 91 in real time. The surgeon 101 can then have a precise idea of the orientation of his or her tools with respect to the vertebra.

In an embodiment, the system is interactive and allows the surgeon 101 to give oral instructions, for example "Display vertebra L5" so that the computer displays the image corresponding to vertebra L5.

Figure 10:
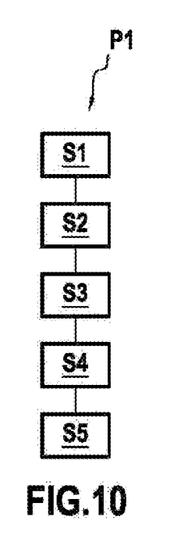
FIG. 10 shows a flow chart of a preoperative phase.
Figure 11:
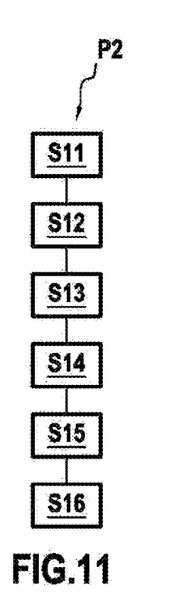
FIG. 11 shows a flow chart of a perioperative phase.

FIG. 10 shows a flow chart of a preoperative phase P1, and FIG. 11 shows a flow chart of a perioperative phase P2.

Phase P1 comprises the steps S1 to S5. In step S1, an image I of at least one operating area ZO is taken, for example by tomodensitometry means. In step S2, at least three reference points R1, R2, R3 are determined and recorded in the case of a dynamic system, or simply noted in the case of a static system. In step S3, an orientation reference RO, as described above in relation to FIG. 4, is calculated by means of the reference points and then recorded or noted. In step S4, at least one direction vector [V]ro is determined for the surgical movement to be performed and then recorded or noted. In step S5, the process is repeated if necessary for other operating areas.

Phase P2 comprises the steps S11 to S16. In step S11, the operating area ZO is exposed. In step S12, a point of the ancillary instrument is placed on the first reference point R1. In step S13, another point of the ancillary instrument is placed on the second reference point R2. In step S14, the contact area of the ancillary instrument is placed on the third reference point R3. In step S15, the orientation reference RO of the operating area ZO is determined and communicated, allowing calculation of the rotation matrix Mrors and the direction vector [V]rs. In step S16, the surgical tool is used for performing a surgical movement according to the calculated direction vector.

Figure 12:
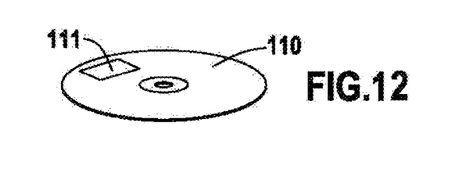
FIG. 12 shows a non-transitory medium which can be read by a computer and comprising a program of computer-executable instructions.

FIG. 12 shows a non-transitory medium 110 which can be read by a computer and comprising a program of computer-executable instructions 111. The program of instructions can comprise the calculation algorithm described in relation to FIG. 4.

Embodiments moreover relate to an assembly or "kit" of at least two ancillary instruments 20, 20', 50, each ancillary instrument being designed for operating areas ZO that are different from one another, for example having different dimensions, different angles between the branches, etc. This allows a range of anatomical variations to be covered. In an embodiment, the ancillary instruments 20, 20', 50 have different sizes, for example small, medium, and large.

It will be understood by a person skilled in the art that the embodiments described above can be modified.

For example, the communication means 25, 35, 45, 55, 65 can be a digital screen, light-emitting diodes ("LED") for example green, orange and red which light up, wired connections (a cable connected to the surgical tool or to the data processing device), wireless connections (Wi-Fi, NFC, Bluetooth, etc), an auditory signal and, more generally, any means for communicating information.

In the above, the contact areas 23, 43, 53, 63 have been described as essentially planar areas which are placed on a tangential contact area ZT. (By "essentially planar" is meant that the area is more or less planar within production limits). Nevertheless, it will be understood by a person skilled in the art that these contact areas can have any other shape designed for coming into contact with a determined area. For example, they can be concave in order to be placed on a rounded shape, such as the spinous process 5, convex in order to be placed in a depression, etc.

In an embodiment, not shown, a tool for determining and communicating a orientation reference is fixed on the operating area ZO itself in order to permanently verify its position, for example in order to ensure that the patient has not moved during the operation, for very delicate operations.

The position of the patient, and more particularly of the operating area, can be adjusted until the correct orientation is found. Means (straps, clamps, etc.) for holding the operating area (the patient) in a given position can be utilized, either before the operation, or during the operation.

It will be understood by a person skilled in the art that certain elements described in relation to an embodiment (for example the determination and communication means, the "MEMS", the spikes, etc.) can be applied to other embodiments.

The surgical tool is for example a perforator, a screwdriver and, in general, any tool that allows a surgical procedure to be performed.

The materials used for the ancillary instrument and the surgical tool can, preferably, be sterilized and pose no biocompatibility problem.

As mentioned above, in certain embodiments, it is not obligatory that the surgical tool is equipped with means for determining and communicating positions. In certain cases, once the orientation reference RO has been obtained, the surgeon can easily determine himself the correct angle, for example an angle of 90° with respect to the orientation reference of the ancillary instrument.

In certain embodiments, the branches of the ancillary instrument 20, 20', 50 can be articulated about the central area, for example by means of hinges arranged between the central area and each branch.

Finally, other methods of calculating the direction vectors can be implemented.

The invention claimed is:

1. An ancillary surgical instrument comprising at least:
   a first contact point to come into contact with a first reference point of an operating area, the first contact point arranged in the form of a first straight edge of a first branch;
   a second contact point intended to come into contact with a second reference point of the operating area, the second contact point arranged in the form of a second straight edge of a second branch;
   a contact area intended to come into contact with a third reference point of the operating area, wherein the first contact point arranged as the first straight edge, the second contact arranged as the second straight edge, and the contact area are coplanar;
   a determination means for determining an orientation reference frame of the ancillary instrument in a Galilean orientation reference frame; and
   a communication means for communicating the determined orientation reference frame.

2. The ancillary instrument according to claim 1, in which the first contact point, the second contact point, the contact area, the determination means and the communication means are incorporated into a single part of the ancillary instrument.

3. The ancillary instrument according to claim 1, in which the contact area is a planar tangential area.

4. The ancillary instrument according to claim 1, in which the orientation reference frame of the ancillary instrument allows an orientation reference frame of the operating area to be determined with respect to the Galilean orientation reference frame by means of a rotation matrix.

5. The ancillary instrument according to claim 3, in the form of a Y and comprising:
   a third branch in the form of a handle; and
   a central area having a lower face that forms the tangential contact area.

6. The ancillary instrument according to claim 5, further comprising validating means for validating the tangential contact area.

7. The ancillary instrument according to claim 6, in which the tangential contact area is transparent and arranged in a cross-ruled form and marked in order to allow a surgeon to determine exactly where the tangential area is in contact with the third reference point.

8. The ancillary instrument according to claim 1, in which the determination means for determining the orientation reference frame is a device comprising at least one of the following components:
   a tri-axial accelerometer;
   a tri-axial magnetometer; and
   a tri-axial gyroscope.

9. The ancillary instrument according to claim 1, in which the determination means for determining the orientation reference frame is a device comprising at least three non-aligned optical markers, intended to be visible by at least one camera filming the operating area.

10. The ancillary instrument according to claim 1, in which the communication means for communicating the orientation reference frame is a visual display.

11. The ancillary instrument according to claim 1, in which the communication means for communicating the orientation reference frame is a wired or wireless connection.

12. A kit comprising at least two ancillary instruments according to claim 1, the ancillary instruments being designed for operating areas that are different from one another.

13. Surgical A surgical orientation system comprising at least one ancillary instrument according to claim 1 and a surgical tool comprising:
   a determination means for determining an orientation reference frame of the tool; and
   a communication means for communicating the orientation reference frame of the tool.

14. The surgical orientation system according to claim 13, in which the ancillary instrument and the surgical tool are capable of being coupled to one and the same device for determining and communicating the orientation reference frame.

15. An operating theatre equipped with an ancillary surgical instrument according to claim 1 and with a device for displaying images and data processing comprising:
   a screen for displaying images taken of the operating area;
   a processor;
   means for entering and manipulating data; and
   means for receiving the data communicated by the ancillary instrument.

16. A preoperative preparation process of a surgical operation, comprising the steps of:
   taking at least one three-dimensional image of an operating area;
   determining at least three reference points of the operating area from the three-dimensional image;
   calculating an orientation reference frame by means of the reference points, the orientation reference frame being subsequently identifiable by an ancillary instrument according to claim 1; and
   determining at least one local orientation reference frame for the surgical operation to be performed.

17. A non-transitory computer readable medium which can be read by a computer and comprising a program of computer-executable instructions for carrying out the process according to claim 16.

18. The ancillary instrument according to claim 1, wherein the first and second contact points, the contact area and the determination means for determining an orientation reference frame are integral.

* * * * *